United States Patent [19]

Hufford et al.

[11] Patent Number: 4,965,272
[45] Date of Patent: Oct. 23, 1990

[54] ANTIMICROBIAL COMPOUND AND COMPOSITIONS PARTICULARLY EFFECTIVE AGAINST CANDIDA ALBICANS

[76] Inventors: Charles D. Hufford; Alice M. Clark, both of Rte. 6, Box 306, Oxford, Miss. 38655

[21] Appl. No.: 218,986

[22] Filed: Jul. 14, 1988

[51] Int. Cl.$^5$ .......................................... A61K 31/435
[52] U.S. Cl. .................................................... 514/288
[58] Field of Search ...................... 546/70, 66; 514/288

[56] References Cited

PUBLICATIONS

Rao et al., "Sampangine, A New Alkaloid ... ", Journal of Nat. Prod., vol. 49, No. 2, pp. 346–347 (1986).
Taylor, "Constituents of Eupometta Species", Austrlian Journ. Chem., 37, pp. 1095–1104 (1984).
Read et al., "Constit. of Eupometia Species", Austrlian Journ. Chem., 32, pp. 2317–2321 (1979).
Bowden et al., "Constit. of Eupomatia Species", Australian Journ. Chem. 29, pp. 2681–2702 (1975).
(I) Leboeuf et al., "Alkaloids of Annonaceae", Chem. Abs., vol. 87(3), entry #87:235826 (1977).
Hufford et al., "Anticandidal Activity of Eupolauridine", Journ. Nat. Prod., vol. 50, No. 5, pp. 961–964 (1987).
Waterman et al., "Chem. of Annonacease", Chem. Abs., vol. 103 (3), entry No. 103:19823n (1985).
Tadic et al., "Kinabaline ... ", Bio. Abs., vol. 83, No. 9, entry #89433 (1987).
Leboeuf etal. (II), "Alkaloids of Annonaceae", Chem. Abs., vol. 83, No. 13, entry #83:111113x (1975).

Primary Examiner—Mukund J. Shah
Assistant Examiner—E. C. Ward
Attorney, Agent, or Firm—William D. Stokes

[57] ABSTRACT

The use of the naturally occurring and readily synthesized alkaloid compound eupolauridine as an antimicrobial agent and particularly against Candida albicans organism.

3 Claims, No Drawings

ANTIMICROBIAL COMPOUND AND COMPOSITIONS PARTICULARLY EFFECTIVE AGAINST CANDIDA ALBICANS

FIELD OF THE INVENTION

This invention is directed to the new antimicrobial, eupolauridine, compositions thereof and a method of providing effective protection against pathological conditions in mammals particularly those caused by *Candida albicans*. The compound and compositions of the invention provide a simple, practical and naturally occurring drug which may be effectively administered alone or in admixture with known non-toxic pharmaceutically-acceptable diluent carriers. The compound of the invention is naturally occurring and readily extracted from the root bark of the West African tree, *Cleistopholis patens* (Benth) Engl. and Diels (Annonaceae). The compound may also be simply and practically synthesized relatively inexpensively.

SUMMARY AND BACKGROUND OF THE INVENTION

*Candida albicans* is a pathogenic yeast fungus which can cause severe and resistant to treatment infections in mammals, for example, moniliasis of the mouth. Infections (candidiasis) caused by *Candida albicans*, are extremely resistant to treatment but, under normal conditions, rarely fatal. On the other hand, *Candida albicans* is an opportunistic and dangerous organism should it infect persons having compromised immune systems such as, for example, AIDS patients and cancer patients undergoing chemotherapy. Under such circumstances, an infection by *Candida albicans* can become quite fatal. Prior to this invention, the principal and, substantially only, treatment of choice for *Candida albicans* has been the drug amphotericin-B. As well known in the art, treatment with amphotericin-B has a great many disadvantages causing numerous and, quite serious, adverse side effects. In humans, the side effects include, under varying conditions, fever, anorexia, nausea and vomiting, diarrhea, muscle and joint pain, phlebitis and thiophlebitis, anemia, abnormal renal function, anuria, cardiovascular distress, hypertension and hypotension.

There has been a continuing search and extensive efforts made to discover a new and clinically useful agent against *Candida albicans* which may be used as an alternative to amphotericin-B. In accordance with the invention, it has been discovered that the compound, and therapeutic compositions comprising, eupolauridine, a naturally occurring compound extracted from the stem and root bark of the tree *Cleistopholis patens* (Benth.) Engl. and Diels (Annonaceae), has remarkable anticandidal activity.

The discovery and extraction of eupolauridine from the tree found throughout West Africa, and its possibly remarkable anticandidal properties, was reported in the Journal of Natural Products, Vol. 50, No. 5, pp. 961-964, Sept.-Oct. 1987, by Hufford, Shihchih Liu, Clark and Babajide Oguntimein.

The invention is the compound eupolauridine compositions thereof, and the method of treatment against *Candida albicans* comprising administering eupolauridine in a therapeutically effective dose. Treatment may be by any of the conventional routes of administration, for example, oral, intramuscular, intravenous, or rectally. The compound of the invention is preferably administered in combination with a pharmaceutically acceptable carrier which may be solid or liquid, dependent upon choice and route of administration. Examples of acceptable carriers include, but are not limited to, starch, dextrose, sucrose, lactose, gelatin, agar, stearic acid, magnesium stearate, acacia, and similar carriers. Examples of liquids include water, edible oils, e.g. peanut and corn.

When administered in solid form, the compound and diluent carrier may be in the form of tablets, capsules, powders, lozenges, suppositories prepared by any of the well known methods. When given as a liquid preparation, the mixture of active compound and liquid diluent carrier may be in the form of a suspension administered as such. The compound is administered in a non-toxic dosage concentration sufficient to inhibit the growth and/or destroy the *Candida albicans* organism. The actual dosage unit will be determined by such generally recognized factors as body weight of the patient and/or severity and type of pathological condition the patient might be suffering with prior to becoming infected with the *Candida albicans* organism. With these considerations in mind, the dosage of a particular patient can be readily determined by the medical practitioner in accordance with the techniques known in the medical arts.

DETAILED DESCRIPTION OF THE INVENTION

It was surprisingly discovered that an alcoholic extract of dried, ground root bark of the tree *Cleistopholis patens* exhibited anticandidal activity. The alcoholic extract was partitioned between chloroform and water and the active chloroform extract was chromatographed using chloroform and a stepwise gradient of increasing percentage of methyl alcohol/chloroform as eluent. The fractions obtained were concentrated on the basis of anticandidal activity exhibited. Further purification of the concentrated fractions, based upon anticandidal activity, resulted in the isolation of the active component identified as the alkaloid, eupolauridine.

Eupolauridine has the structural formula:

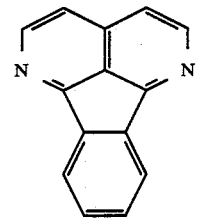

Eupolauridine may be simply and readily prepared by the method of Bowden et al., Aust. J. Chem., 28, 2681 (1975). Following the published procedure eupolauridine for *in vivo* studies was prepared as follows:

To a stirred, cooled (0°) solution of ethyl benzoylacetate (200 g) and concentrated ammonia in ethanol (1 L) was added crotonaldehyde (110 g) at a rate 2.5 ml/min while the temperature was kept below 10°. The mixture was warmed to room temperature overnight and concentrated in vacuo to give a yellow oily residue (260 g). The residue was treated with a mixture of con $H_2SO_4$ (100 ml), con $HNO_3$ (130 ml) and water (580 ml) and the mixture cautiously heated on a steam bath until the evolution of $NO_2$ had subsided, then heated for another 30 min. After cooling, the supernatant was basified with con $NH_4OH$ and extracted with diethyl ether (300 ml×10). The combined ether extracts were concentrated to leave a dark brown oily residue (38 g). Purification of the residue by silica gel column chromatography (70–230 mesh, 400 g, 42×5 cm, three times) using n-hexane-ethyl acetate (2:1) as eluent afforded 15 g of ethyl-4-methyl-2-phenylnicotinate. Hydrolysis of ethyl-4-methyl-2-phenylnicotinate (15 g) with refluxing ethanolic KOH, followed by work-up afforded 4-methyl-2-phenylnicotinic acid (9 g) as colorless prisms, mp 210–212°. Treatment of 4-methyl-2-phenylnicotinic acid (9 g) with polyphosphoric acid (166.7 g) at 130° for 3 hr., afforded 1-methyl-4-azafluoren-9-one (7.5 g) as yellow prisms from n-hexane, mp 130–131° C.

To a stirred mixture of t-BuOK (4.3I g) and dry dimelhoxyethane (75 ml) (0° under nitrogen) was added a solution of 1-methyl-4-azafluoren-9-one (5g) in dimethoxyethane (75 ml). After 2 min, a solution of diethyl oxalate (5 g) in dimethoxyethane (75 ml) was added and stirring was continued for 15 hr at room temperature. The suspension was diluted with ether, the precipitate collected, washed with ether, dried, dissolved in cold water and acidified to pH 6 with 3N HCl. The red gelatinous precipitate was collected, washed thoroughly and dried. Crystallization from methanol afforded ethyl-9-oxo-4-azafluoren-1-ylpyruvate (2.9 9) as small yellow prisms, mp 196–197°. Treatment of ethyl-9-oxo-4-azafluoren-1-ylpyruvate (2.9 g) with a saturated solution of ethanolic ammonia (90 ml) in an autoclave at 100° for 3 hr., followed by work-up and crystallization from methanol afforded 1,6-diazafluoranthene-2-carboxamide (0.9 g) as small yellow prisms, dec. 300°. Hydrolysis of 1,6-diazafluoranthene-2-carboxamide in refluxing ethanolic KOH afforded 1,6-diazafluoranthane-2-carboxylic acid (0.7 g), which was decarboxylated by heating at 300° C. for 10 min. After cooling, the residue was dissolved in ether, filtered and evaporated to give a yellowish-brown residue (0.2 g). Chromatography of the residue over silica gel using n-hexane-ethyl acetate (1:1) as eluent afforded eupolauridine (0.1 g) as fine yellow needles, mp 152–153° (lit. mp 156–157°, Bowden, et al. 1975. *Aust. J. Chem.* 29:2681). Ultimately the synthesis was repeated to afford 1 g. of eupolauridine for in vivo studies. The overall yield of eupolauridine from ethyl-4-methyl-2-phenylnicotinate is approximately 4%.

The eupolauridine of the invention and compositions thereof were discovered to exhibit a remarkable zone of inhibition against three test strains of *Candida albicans*. The minimum inhibitory concentration (MIC) of eupolauridine was found to be 1.56 µg/ml for each of the three pathogenic strains in yeast-nitrogen broth.

In vitro evaluation of the anticandidal activity of the inventive compound and compositions was carried out using the agar-well diffusion assay as follows:

*Candida albicans* NIH B311 used to induce experimental disseminated candidiasis was used for the initial qualitative evaluation of anticandidal activity. The organism was grown in Sabouraud-dextrose broth (SDB) for 14 hours at 37°, at which time the cells were harvested by centrifugation (4°, 2000 rpm, 3 min). After centrifugation, the cells were washed and suspended in sterile 0.9% saline to give a final concentration of $10^0$ colony forming units (CFU) per ml (adjusted using a hemocytometer). Culture plates (15×100 mm) for the qualitative assay were prepared from 25 ml of Sabouraud-dextrose agar. Using sterile cotton swabs, the plates were streaked with the suspension ($10^0$ CFU/ml of *Candida albicans* B311. Cylindrical plugs were removed from the agar plates by means of a sterile cork borer to produce wells with a diameter of approximately 11 mm. To the well was added 100 µl of solution or suspension of an extract, fraction, or pure compound. Crude extracts and fractions were tested at a concentration of 20 mg/ml, whereas pure compounds were tested at 1 mg/ml. When solvents other than $H_2O$, EtOH, MeOH, DMSO, DMF, or $Me_2CO$ were required to dissolve extracts or compounds, solvent blanks were included. Anticandidal activity was recorded as the width (in mm) of the zone of inhibition following incubation of the plates at 37° for 24 hours. The antifungal agents amphotericin-B and ketoconazole were included as standards in each assay.

The method used to determine the minimum inhibitory concentration (MIC) of the inventive compound was a twofold serial broth dilution assay in yeast nitrogen broth. In addition to *Candida albicans* B311, the MIC values for eupolauridine were also determined for two additional strains of *Candida albicans*: ATCC 10231 and a clinical isolate, designated WH. The inventive compound was initially tested using a concentration of 100 µg/ml in the first tube. The compound was added to sterile Sabouraud-dextrose broth as a solution in DMSO. The inoculum for the MIC determination was prepared as described for qualitative evaluation. Using a calibrated sterile wire loop, 10 µl of the $10^{\neq}$CFU/ml suspension of *Candida albicans* was used as inoculum for each tube. The MIC value was taken as the lowest concentration of compound that inhibited the growth of the test organisms after 24 and 48 hours of incubation at 37°. The antifungal agents amphotericin-B and ketoconazole were included as standards in each screen.

The results of the MIC testing for various pathogenic agents is set out in Table 1.

TABLE I

| Organism | MIC µg/ml Eupolauridine |
| --- | --- |
| *Candida albicans* B311 | 1.56 |
| *Candida albicans* 10231 | 1.56 |
| *Candida albicans* WH | 1.56 |
| *Cryptococcus neoformans* 32264 | 1.56 |
| *Aspergillus flavus* 9170 | 6.25 |
| *Aspergillus fumigatus* 26934 | 6.25 |
| *Trichophyton mentagrophytes* 9972 | 1.56 |
| *Saccharomyces cerevisiae* 9763 | 3.12 |

In the in vivo testing of the inventive compound and compositions, outbred mice were used. A disseminated infection of *Candida albicans* in the test animals was achieved by intravenous injection of 0.5 to $1 \times 10^6$ CFU of the pathogen. The organism is rapidly cleared from the blood and most tissues, except the kidney which is the primary target organ for the disseminated infection in mice. It is known than an inoculum of $0.5 \times 10^6$ CFU will cause death of outbred mice within 10–14 days due to disseminated infection if untreated. The vehicle used for administering the compound of the invention was a mixture consisting of 50% USP water, 40% propylene glycol and 10% absolute ethonol. The results of the in vivo tests are set out in Table II. It will be observed from the results that at 10 days, none of the vehicle-treated infected control animals had survived while 50% of the animals treated with eupolauridine (at a dose of 20 mg/kg body weight) survived, which is not statistically significantly different from the results with amphotericin-B. Chi Square analyses of the data for the tenth day yielded a P value of 0.012 indicating that there is a greater than 95% probability that the groups are significantly different, that is, the survival in drug-treated groups is significantly higher than the vehicle-treated groups.

TABLE II

| Day | Eupolauridine | | | Amphotericin-B | Vechicle |
|---|---|---|---|---|---|
| | 20 mg/kg | 7 mg/kg | 2 mg/kg | 2.5 mg/kg | |
| 1 | 0/10 | 0/10 | 0/10 | 0/10 | 0/10 |
| 2 | 0/10 | 0/10 | 0/10 | 0/10 | 0/10 |
| 3 | 0/10 | 2/10 | 0/10 | 0/10 | 0/10 |
| 4 | 0/10 | 2/10 | 0/10 | 0/10 | 0/10 |
| 5 | 0/10 | 2/10 | 0/10 | 0/10 | 0/10 |
| 6 | 0/10 | 3/10 | 1/10 | 1/10 | 0/10 |
| 7 | 1/10 | 3/10 | 3/10 | 2/10 | 3/10 |
| 8 | 3/10 | 3/10 | 4/10 | 2/10 | 6/10 |
| 9 | 3/10 | 4/10 | 4/10 | 4/10 | 7/10 |
| 10 | 5/10 | 7/10 | 7/10 | 4/10 | 10/10 |

*Number dead/Total

The invention has been described in detail with particular reference to the preferred embodiments thereof, howeVer, it is to be understood that modifications may be made without departing from the spirit and scope of the invention.

We claim

1. An antimicrobial composition consisting essentially of eupolauridine in a therapeutically-effective concentration and a non-toxic, pharmaceutically-acceptable carrier.

2. A method for preventing pathological conditions in mammals brought about by the presence of *Candida albicans* organism comprising administering to said mammals in a therapeutically effective concentration, a composition consisting essentially of eupolauridine and a non-toxic, pharmaceutically-acceptable carrier.

3. A composition effective against *Candida albicans* consisting essentially of eupolauridine in a therapeutically-effective concentration and a non-toxic, pharmaceutically-acceptable carrier.

* * * * *